(12) United States Patent
Hacker et al.

(10) Patent No.: US 7,993,902 B2
(45) Date of Patent: Aug. 9, 2011

(54) **PLASMID-FREE CLONE OF *E. COLI* STRAIN DSM 6601**

(75) Inventors: Jorg Hacker, Gerbrunn (DE); Tobias Oelschlaeger, Kitzinger (DE); Sibylle Oswald, Wurzburg (DE); Ulrich Sonnenborn, Bochum (DE); Hans Proppert, Hagen (DE)

(73) Assignee: Pharma-Zentrale GmbH, Herdecke (DE)

( * ) Notice: Subject to any disclaimer, the term of this patent is extended or adjusted under 35 U.S.C. 154(b) by 220 days.

(21) Appl. No.: 10/525,558

(22) PCT Filed: Jun. 25, 2004

(86) PCT No.: PCT/EP2004/006886
§ 371 (c)(1),
(2), (4) Date: Sep. 2, 2005

(87) PCT Pub. No.: WO2004/113575
PCT Pub. Date: Dec. 29, 2004

(65) Prior Publication Data
US 2006/0094117 A1 May 4, 2006

(30) Foreign Application Priority Data
Jun. 26, 2003 (DE) .................. 103 28 669

(51) Int. Cl.
*C12N 1/20* (2006.01)
*C12N 1/21* (2006.01)
(52) U.S. Cl. .................. 435/252.1; 435/252.3
(58) Field of Classification Search .......... None
See application file for complete search history.

(56) References Cited

U.S. PATENT DOCUMENTS

| 4,686,184 A | 8/1987 | Puhler et al. | 435/172.3 |
| 6,391,631 B1 | 5/2002 | Hacker et al. | 435/320.1 |

FOREIGN PATENT DOCUMENTS

| WO | WO 98/44134 | * 10/1998 |
| WO | WO 99/26642 | * 6/1999 |
| WO | WO 00/78925 | 12/2000 |

OTHER PUBLICATIONS

Kruis et al. Maintaining remission of ulcerative colitis with the probiotic *Escherichia coli* Nissle 1917 is as effective with standard mesalazine. Gut, 53(11): 1617-1623, 2004.*
Trevors et al. Plasmid curing in bacteria. FEMS Microbiol. Reviews 32: 149-157, 1986.*
Uraji et al. A novel plasmid curing method using incompatibility of plant pathogenic Ti plasmids in *Agrobacterium tumefaciens*. Genes Genet. Syst. 77: 1-9, 2002.*
Alexeyev et al. Improved antibiotic-resistance gene cassettes and omega elements for *Escherichia coli* vector construction and in vitro deletion/insertion mutagenesis. Gene 160: 63-67, 1995.*
Gasson et al. Plasmid complements of *Streptococcus lactis* NCDO 712 and other lactic streptococci after protoplast-induced curing. J Bacteriol. Apr. 1983; 154(1): 1-9.*
International Search Report in corresponding PCT application PCT/EP2004/006886, mailed Apr. 10, 2004, 2 pages.
Duval-Iflah Y et al., "Implantation of a strain of *Escherichia coli* in the degestive tract of human newborns: barrier effect against antibioresistant *E. coli*", Annales De Microbiologic, May-Jun. 1982, vol .133, No. 3, May 1982, pp. 393-408.
Kruls W. et al., "Einsatz von Probiotika in der Humanmedizin", Die Medizinische Welt, 1996, pp. 53-57.
Internet search: "Inhibitory effect of probiotic *Escherichia coli* strain Nissle 1917" www.ingenta.com, 1 page.
Instruction pamphlet for Mutaflor (effective substance: *Escherichia coli* strain Nissle 1917), by Ardeypharm GmbH, 4 pages. (in German).
English translation of Instruction pamphlet for Mutaflor (effective substance: *Escherichia coli* strain Nissle 1917), by Ardeypharm GmbH, 3 pages.
Blum et al. "Properties of *Escherichia coli* Strains of Serotype O6", Plasmid, New York, NY, vol. 23, No. 4, Jul. 1, 1995, pp. 234-236.
Cukrowska et al., "Specific Proliferative and Antibody Responses of Premature Infants to Intestinal Colonization with Nonpathogenic Probiotic *E. coli* Strain Nissle 1917", Scand. J. Immunol., vol. 55, No. 2, Feb. 2002, pp. 204-209.
Figueiredo et al. "Influence of oral inoculation with plasmid-free human *Escherichia coli* onthe frequency of diarrhea during the first year of life in human newborns", J. of Pediatric Gastroenterology and Nutrition, Jul. 2001, vol. 33, No. 3, May 1982, pp. 393-408.
Tolker-Nielsen et al. "A statistical analysis of the formation of plasmid-free cells in populations of *Escherichia coli*," J. Bacteriology, Jul. 1994, vol. 176, No. 14, pp. 4306-4310.
Hynes et al., "Direct selection and deletion of *Rhizobium* plasmids using transposons carrying the *Bacillus subtilis* sacB gene", Gene, vol. 78, 1989, pp. 111-120.
Blum-Oehler et al. "Development of strain-specific PCR reactions for the detection of the probiotic *Escherichia coli* strain Nissle 1917 in fecal samples", Research in Microbiology, vol. 154 (2003) pp. 59-66.
Boudeau et al., "Inhibitory effect of probiotic *Eschericia coli* strain Nissle 1917 on adhesion to and invasion of intestinal epithelial cells by adherent-invasive *E. coli* strains isolated from patients with Crohn's disease", Aliment Pharmacol Ther, 2003, vol. 18, pp. 45-56.
Patzer et al., "The colicin G, H and X determinants encode microcins M and H47, which might utilize the catecholate siderophore receptors FepA, Cir, Fiu and IroN", Microbiology (2003), vol. 149, pp. 2557-2570.
Fric et al., "The effect of non-pathogenic *Escherichia coli* in symptomatic uncomplicated diverticular disease of the colon", European Journal of Gastroenterology & Hepatology, 2003, vol. 15, pp. 313-315.
Waidmann et al., "Bacteroides vulgatus protects against *Escherichia coli*-induced colitis in gnotobiotic interleukin-2-deficient mice", Gastroenterology, 2003, vol. 125, pp. 162-177.
Tromm et al., "The probiotic *E. coli* Strain Nissle 1917 for the Treatment of Collagenous Colitis: First Results of an Open-Label Trial", Gastroenterology 2004, vol. 42, pp. 365-369.
Alterhoefer et al., "The pribiotic *Escherichia coli* strain Nissle 1917 interferes with invasion of human intestinal epithelial cells by different enteroinvasive bacterial pathogens", FEMS Immunology and Medical Mimcrobiology, 40 (2004), pp. 223-229.

(Continued)

Primary Examiner — Michele Joike
(74) Attorney, Agent, or Firm — Nash and Titus LLC

(57) ABSTRACT

The invention relates to a plasmid-free clone of *Escherichia coli* strain DSM 6601, to a method for preparing the same and to the use thereof as a cloning vehicle.

6 Claims, 3 Drawing Sheets

OTHER PUBLICATIONS

Schultz et al., "Preventive effects of *Escherichia coil* Strain Nissle 1917 on acute and chronic intestinal inflammation in two different murine models of colitis", Clinical and Diagnostic Laboratory Immunology, Mar. 2004, vol. 11, No. 2, pp. 372-378.

Otte et al., "Functional modulation of enterocytes by gram-positive and gram-negative microorganisms", Am J. Physiol. Gastrointest. Liver Physiol., vol. 286, 2004, pp. G613-G626.

Grozdanov et al., "Analysis of the genome structure of the nonpathogenic probiotic *Escherichia coli* Strain Nissle 1917", vol. 186, No. 16, Aug. 2004, pp. 5432-5441.

Henker et al., Pediatric Gastroenterology, Hepatology and Nutrition, "Maintenance Therapy of Ulcerative Colitis in Children and Teenagers wit lithe Probiotic *E. coli* Strain Nissle 1917", 2. Weltkongress of Jul. 3-7, 2004, pp. 523-527.

Wehkamp et al., "NF-kB- and AP-1-mediated induction of human beta defensin-2 in intestinal epithelial cells by *Escherichia coli* Nissle 1917: a novel effect of a probiotic bacterium", Infection and Immunity, Oct. 2004, vol. 72, No. 10, pp. 5750-5758.

von Buenau et al., "*Escherichia coli* Strain Nissle 1917: significant reduction of neonatal calf diarrhea", J. Dairy Sci, vol. 88, 2005, pp. 317-323.

Cross et al, "Patterns of cytokine induction by gram-positive and gram-negative probiotic bacteria", FEMS Immunology and Medical Microbiology, vol. 42, pp. 173-180, 2004.

* cited by examiner

PLASMID-FREE CLONE OF *E. COLI* STRAIN DSM 6601

BACKGROUND OF THE INVENTION

The invention relates to a plasmid-free clone of *E. coli* strain DSM 6601, a method of its preparation and the use of the bacteria obtained in this manner as a cloning vehicle.

*E. coli*, a bacteria that occurs in nature, especially in the intestines of humans and animals, has long been the subject of intensive microbiological and genetic engineering research and is used in genetic engineering in particular for cloning and/or expressing certain genes and/or proteins.

Most strains of the genus *Escherichia* are pathogenic outside of the lumen of the bowels and generally cause infections at the affected sites. A non-pathogenic strain of the genus *Escherichia coli* is the strain DSM 6601 deposited in the German Collection for Microorganisms, that deviates in a few genetic features from all other *E. coli* strains. However, it turned out that this strain can be manipulated genetically only under difficult circumstances and partially not at all and therefore cannot be used as a simple cloning means.

*E. coli* DSM 6601 naturally contains two plasmids designated as pMut1 or pMut2 that have a size of 3177 and 5552 kb. These plasmids and their DNA sequences are described, e.g., in U.S. Pat. No. 6,391,631.

The *Escherichia coli* strain having accession number DSM 6601 was deposited under the terms of the Budapest Treaty on Jul. 11, 1991 in the German Collection for Microorganisms, DSMZ-Deutsche Sammlung von Mikrooganismen and Zellkulturen GmbH, located at Mascheroder Weg 1b, D-38124, Braunschweig, Germany.

SUMMARY OF THE INVENTION

Starting with the consideration that the pathogenicity and non-pathogenicity of *E. coli* bacteria are obviously partially controlled by their plasmids, and with the consideration that the partially occurring "genetic resistance" of *E. coli* strains might also be connected to its cryptic plasmids, the invention addresses the basic problem of developing a plasmid-free *E. coli* strain that is otherwise genetically totally identical to the additional strain as regards its genomic DNA.

The above problem is solved by making available a plasmid-free clone of *E. coli* strain DSM 6601 and by a method of preparing such a clone.

DETAILED DESCRIPTION

Figure 1:
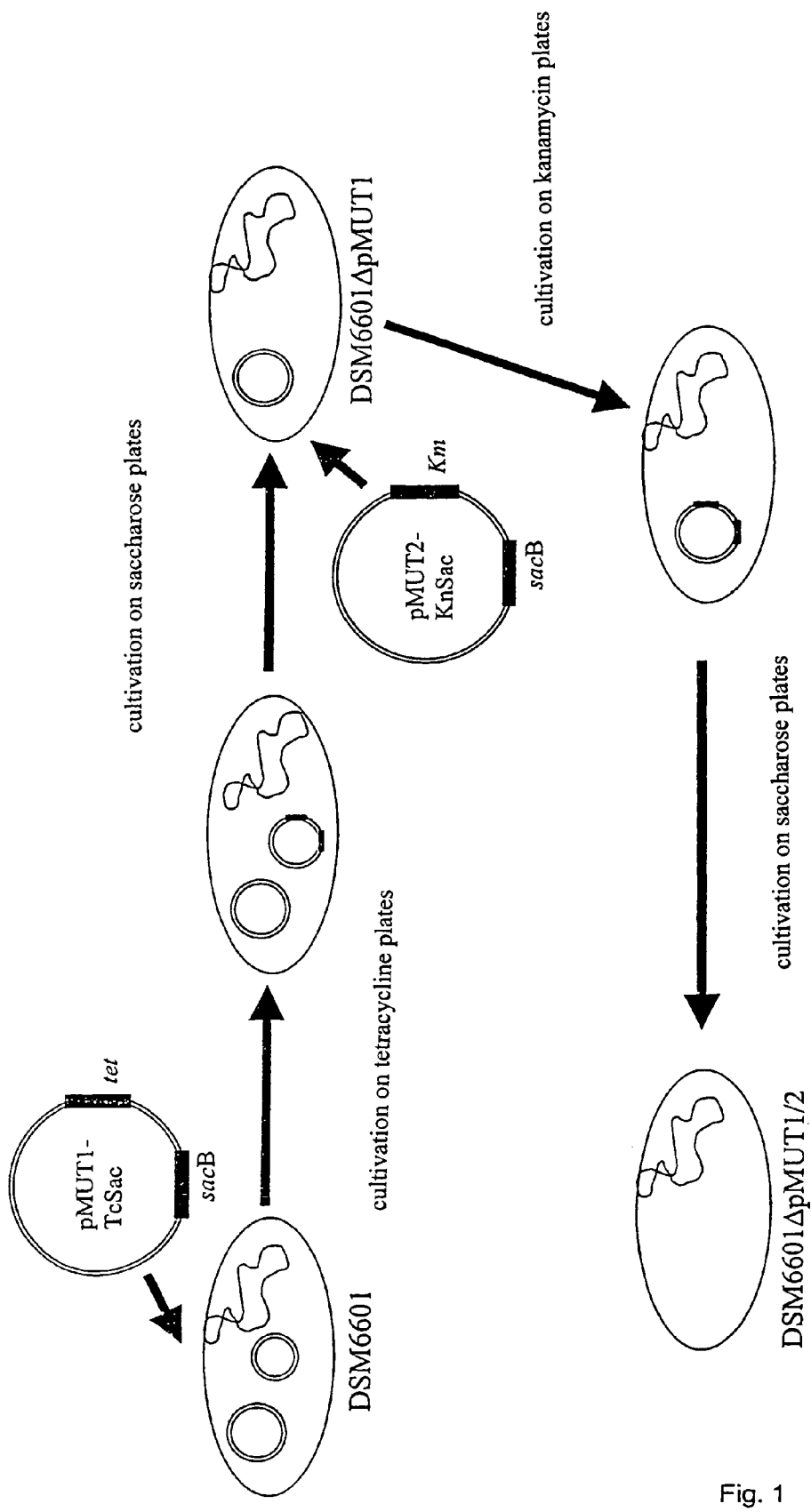
FIG. 1 shows a schematic of the method for preparing the plasmid-free clone of strain DSM 6601.

It turned out in the exhaustive investigations that led to the present invention that plasmid-free clones of strain DSM 6601 cannot be prepared at all with normal genetic engineering methods or can be prepared only with great difficulty so that special paths must be taken in order to generate such clones. Since the wild type of the strain has two plasmids of different sizes in addition to its genomic DNA, the elimination of these plasmids must take place in several steps that take place in part in parallel.

The plasmid-free *Escherichia coli* strain DSM 6601 of this invention was deposited on Sep. 14, 2004, under the terms of the Budapest Treaty, in the German Collection for Microorganisms, DSMZ Deutsche Sammlung von Mikroorganismen and Zellkuturen GmbH, Mascheroder Weg 1b, D-38124 Braunschweig, Germany, and granted the accession number of DSM 16700.

In order to prepare the clones in accordance with the invention the plasmids pMut1 and pMut2 occurring naturally in *E. coli* strain DSM 6601 are marked in accordance with the method of the invention in a first step with an antibiotic resistance. To this end the plasmids are isolated according to traditional methods and the resistance gene inserted at the desired site. According to a preferred embodiment the resistance gene is inserted into the particular plasmid together with an expression cassette containing a promoter that can be constitutive or also inducible.

Plasmids obtained in this manner are then introduced into a suitable host according to traditional methods, e.g., the $CaCl_2$ method or electroporation where they are cloned, during which the resistance gene inserted into the particular plasmid facilitates the selection of the host cells carrying the plasmid. A host suitable for cloning the plasmid carrying a resistance gene is, e.g., the *E. coli* strain DH5α or *E. Coli* HB101.

The plasmids carrying the resistance gene are isolated and the sacB gene is subsequently introduced into the plasmids in order to make another marker available.

The plasmids obtained and marked in this manner are then introduced into *E. coli* strain DSM 6601.

After transformation the *E. coli* DSM 6601 are cultivated on a medium containing the antibiotic/antibiotics for which the resistance genes introduced in the preceding steps into the plasmids impart resistance.

By cultivating in such a medium, only clones grow that are resistant to the antibiotics contained in the nutrient medium. Furthermore, the bacteria lose excess genetic material since they no longer require the original plasmids pMut1 and pMut2 for their growth so that the bacteria finally contain only the modified plasmas pMut1 and pMut2 (that contain the resistance gene/genes and the sacB gene).

In a further step the bacteria cultivated in this manner are transferred into a nutrient medium that inhibits the growth of bacteria containing the sacB, during which a selection pressure is exerted that substantially only permits the growth of bacteria that have lost the plasmid carrying the sacB gene. This can take place by cultivating the strain at 30° C. in the presence of 10% saccharose, since under such conditions only those clones can replicate that have lost the plasmid carrying the sacB gene.

As a consequence, a plasmid-free derivative of strain DSM 6601 is obtained. It was now found that the clones in accordance with the invention, with the condition of the loss of the plasmids, did not experience any change of the genomic DNA and can surprisingly be readily used as cloning vehicles.

Thus, they can be safely used in the laboratory as host cell for the cloning and expression of a plurality of genes and proteins. Experiments with strain DSM 6601 ΔpMut1/2 have shown that it is an especially good acceptor for foreign DNA when the latter is integrated into its own plasmids present in isolated form, that is, therefore its own plasmids function as cloning vectors for the foreign DNA. Furthermore, since they are derived from a non-pathogenic strain, they can be used for the treatment of disturbances of the gastrointestinal tract in animals and humans. To this end they can be transformed, if desired with foreign genes that further the adhesion of the bacteria to the mucosa such as, e.g., adhesines that further the adhesion of the bacteria, optionally host-animal specifically, to the mucosa of, e.g., cattle and/or swine and thus hinder or prevent the growth of other pathogenic microorganisms.

The present invention will now be explained in detail with reference made to the examples.

Example 1

Modification of pMut 1

The two naturally occurring plasmids pMut1 and pMut2 of wild type isolated in accordance with the plasmid midi-prep protocol of QIAGEN (QIAGEN Plasmid Purification Handbook 12/2002, pages 16-20).

The tetracycline resistance cassette derived from vector pBR322 was selected for marking the plasmid. The associated promoter was taken from plasmid pASK75. The plasmid resulting from this cloning was designated by pKS-tetA$^{tetp/o}$. The insert tetA$^{tetp/o}$ (insert size 1 0.5 kb) was cut out with restriction enzymes XbaI and HindIII. The XbaI/HindIII fragment was introduced into plasmid pMut1 via a NdeI restriction site.

To this end the restriction batch was purified via a column (QuIagen, PCR purification kit) after restriction digestion of the plasmids with the appropriate enzymes and subjected to a Klenow treatment in order to form blunt ends. In order to prevent a religation of the plasmid pMut1 a dephosphorylation of the plasmid linearized with restriction enzyme NdeI and treated with Klenow enzyme was carried out. Subsequently, the vector pMut1 and the insert tetA$^{tetp/o}$ were litigated and the E. coli K-12 strain DH5α transformed therewith.

In order to prepare competent cells 150 mm LB medium (Lurea-Bertani medium) was inoculated with 1.5 mm of a ÜN culture and agitated at 37° C. until an OD$_{600}$=0.5. The bacterial culture was then incubated 20 minutes on ice and centrifuged 10 minutes with 4000 rpm at 4° C. The bacterial pellet was washed 3 times in sterile, ice-cold 10% glycerol, at first with 100%, then with 50% and finally with 10% of the initial volume. Finally, the washed pellet was re-suspended in 300 μl 10% glycerol, aliquoted (40 μl) and stored at −80° C. For the transformation of bacterial cells 1-2 μl plasmid DNA (1-100 ng) was mixed with 40 μl competent cells thawed on ice and incubated 5 minutes on ice. This batch was then pipetted free of air bubbles between the two electrodes of a sterile and pre-cooled 2 mm electroporation cuvette. The cuvette was dried off well and inserted into the electrode holder. After the electrical impulse had been performed at 2.5 kV, 200Ω and 25 μF the bacterial suspension was washed out of the cuvette with 1 mm LB medium and incubated at 37° C. for 1-2 hours in an agitator. The bacteria were subsequently centrifuged off and the supernatant drawn off up to 100 μl. The sediment was re-suspended in the remaining 100 plated out onto a Tc-containing selection plate and incubated ÜN (overnight) at 37° C.

Figure 2:
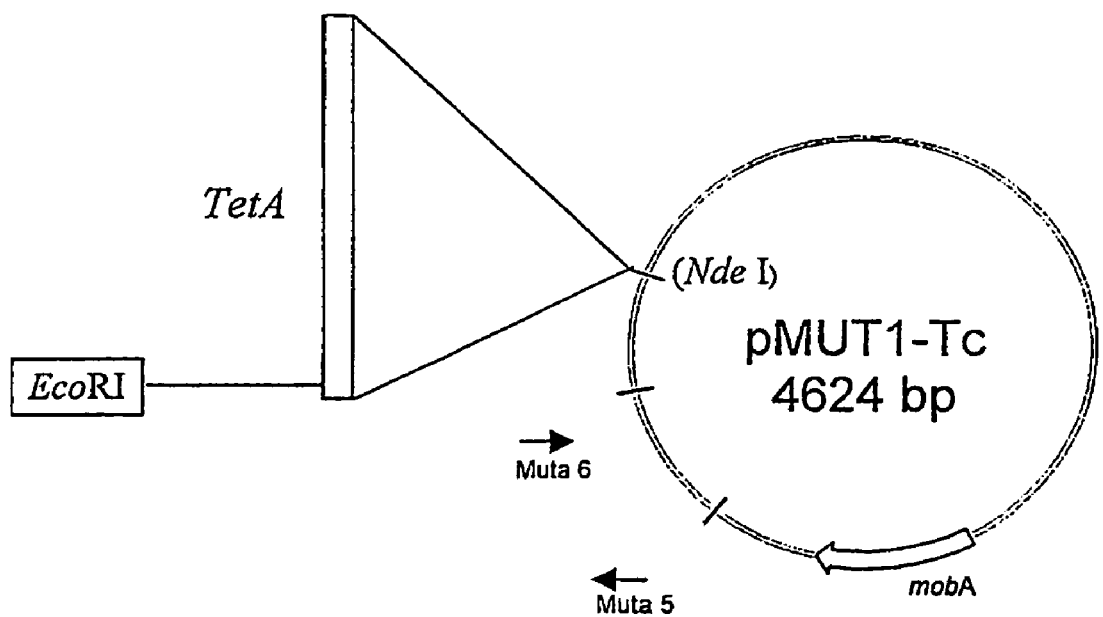
FIG. 2 shows the physical map of plasmid pMut1-Tc.

The success of the cloning was tested by minipreparation of the particular plasmid of individual bacterial clones. The plasmid pMut1 marked with the tetracycline cassette was designated as pMut1-Tc. FIG. 2 shows the physical map of plasmid pMut1-Tc. It indicates the insertion site (originally a singular NdeI site) for the DNA fragment that imparts tetracycline resistance. This DNA fragment also contains the singular Eco-RI sequence suitable for clonings. Furthermore, the binding sites for the primers muta 5 and muta 6 are indicated that are suitable for the specific demonstration of this plasmid by PCR.

Example 2

Modification of pMut2

A kanamycin resistance cassette was selected for the marking of plasmid pMut2 that was derived from vector pACYC177. To this end the resistance cassette (size 1 0.34 kb) was cut out of the latter with the restriction enzyme StuI and introduced via a BglII restriction cleavage site into plasmid pMut2. After restriction digestion of the plasmids with the appropriate enzymes the restriction batch was purified via a column (Quiagen PCR fraction kit) and plasmid pMut2 subjected to a Klenow treatment in order to form blunt ends for the cloning. In order to avoid a religation of plasmid pMut2 a dephosphorylation linearized with restriction enzyme Bg/II and treated with Klenow enzyme was carried out. Subsequently, vector pMut2 and the kanamycin cassette were litigated and the E. coli K-12 strain DH5α transformed as described in example 1. The transformation was plated out onto Kn-containing LB agar plates. The success of the cloning was tested by minipreparation of plasmid DNA of individual bacterial clones. Plasmid pMut2 marked with the kanamycin cassette was designated as pMut2-Kn.

Figure 3:
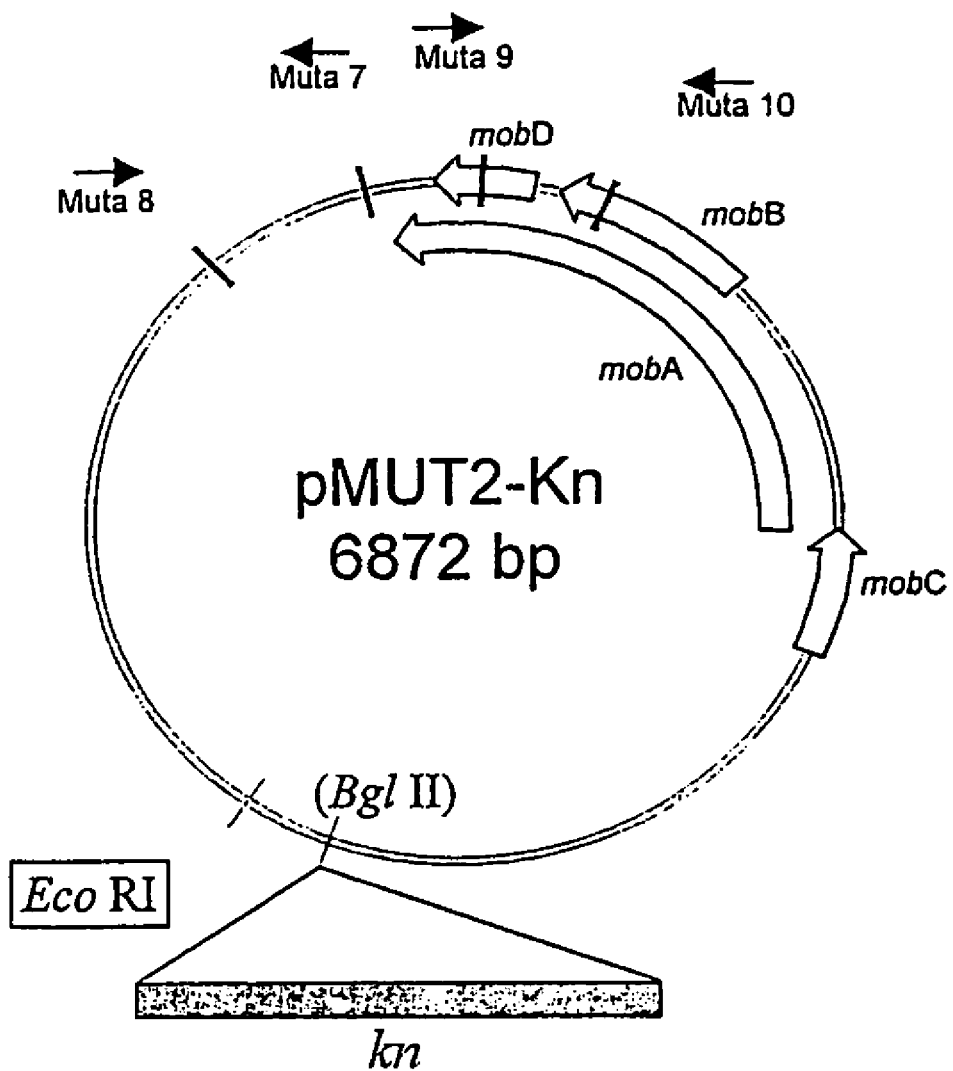
FIG. 3 shows the physical map of plasmid pMut2-Kn.

FIG. 3 shows the physical map of plasma pMut2-Kn. The insertion site (originally a BglII site) for the kanamycin resistance cassette as well as the singular Eco-RI sequence suitable as cloning site are sketched in. Muta 7 to Muta 10 characterize those areas complementary to the sequences of the primers that are suitable for the specific demonstration of this plasmid by PCR.

Example 3

Introduction of the sacB Gene

In order to introduce the sacB gene (coded for a Levan saccharose) into the plasmids pMut1-Tc and pMut2-Kn, the particular singular Eco-RI restriction cleavage site was selected in both plasmids. The sacB gene (size 2 0.6 kb) was isolated from the plasmid pCVD442 with the restriction enzyme PstI. In order to prepare the vectors pMut1-Tc and pMut2-Kn, these plasmids were linearized with Eco-RI and subsequently submitted to a Klenow treatment and dephosphorylated in order to form blunt ends. The insert sacB was purified with PstI after the restriction digestion and treated with Klenow enzyme. The linearized vectors and the insert were ligated and the E. coli K-12 strain DH5α, that was rendered competent as described in example 1, was transformed therewith. The success of the cloning was checked by minipreparation of plasmid DNA of individual bacterial clones and subsequent restriction analysis. The plasmids pMut1-Tc and pMut2-Kn marked with the sacB gene were designated as pMut1-TcSac and pMut2-KnSac.

Example 4

Preparation of a Plasmid-Free Clone of E. coli Strain DSM 6601

At first the plasmid pMut1-TcSac was transformed by electroporation into this strain as described in example 1. After the electroporation in order to transfer plasmid pMut1-TcSac into strain DSM 6601 the batch was plated out onto LB plates containing Tc (50 μg/ml). The tetracycline-resistant bacterial clones obtained were checked for the possession of plasmid pMut1-TcSac and the associated loss of the naturally occurring plasmid pMut1. The loss of plasmid pMut1 was demonstrated after preparation of the plasmid DNA and restriction digestion of the same with the enzyme Eco-RI after electrophoretic separation of the linearized plasmids by the lack of the DNA bands representing pMut1.

Subsequently, one of these clones was attracted overnight in LB medium with 10% saccharose at 30° C. and then plated out onto LB plates with 10% saccharose (LB medium consists of 10 g peptone from casein, 5 g yeast extract and 5 g sodium chloride per 1 l distilled water). Saccharose-containing LB medium was prepared in that a part of a sterilely filtered, 50% (wt./vol.) saccharose stock solution was added to the autoclaved medium after it had cooled off to 45° C. up to an end concentration of 10%). The plates were incubated at 30° C. Under these conditions only those clones can replicate that no longer express sacB, that is, they have lost the plasmid carrying the sacB gene. The resulting strain DSM 6601ΔpMut1 was checked for the loss of plasmid pMut1-TcSac.

Then, plasmid pMut2-KnSac was introduced by electroporation into strain DSM 6601ΔpMut1.

After the electroporation in order to transfer plasmid pMut2-TcSac into strain DSM 6601ΔpMut1, the batch was plated out onto LB plates containing Kn (50 µg/ml). The kanamycin-resistant bacterial clones obtained were checked for the possession of plasmid pMut2-KnSac and the associated loss of the naturally occurring plasmid pMut2. Subsequently, one of these clones was attracted overnight in LB medium with 10% saccharose at 30° C. and then plated out onto LB plates with 10% saccharose. The plates were incubated at 30° C. The resulting strain DSM 6601 ΔpMut1/2 was checked for the loss of plasmid pMut2-KnSac.

Furthermore, a Pulsfeld gel electrophoresis of the plasmid-free strain DSM 6601 ΔpMut1/2 was carried out in order to exclude any chromosomal modifications of the strain. It was determined that no changes could be demonstrated and further examinations showed that the plasmid-free clone displayed no morphological, biochemical or fermentative changes.

The invention claimed is:

1. A plasmid-free clone of *Escherichia coli* strain DSM 6601, which strain is identified as having accession number DSM 16700.

2. The method of preparing a plasmid-free clone according to claim 1, comprising the following steps:
   a) introducing a resistance gene into plasmids pMut1 and pMut2,
   b) introducing the sacB gene into the plasmids obtained in step a) so as to produce a pMut1 plasmid carrying a resistance gene and a sacB gene, and a pMut2 plasmid carrying a resistance gene and a sacB gene,
   c) introducing the altered pMut1 and pMut2 plasmids obtained in step b) into the *Escherichia coli* strain DSM 6601, and cultivating the strain obtained thereby under conditions in which the naturally occurring pMut1 and pMut2 plasmids are displaced by the altered pMut1 and pMut2 plasmids obtained in step b); and
   d) cultivating the clones obtained in step c) that substantially only permit the growth of bacteria that lack the sacB gene, so that the *Escherichia coli* containing the altered pMut1 and pMut2 plasmids do not grow, and thereby is produced a plasmid-free clone of *Escherichia coli* strain DSM 6601.

3. The method according to claim 2, characterized in that the resistance genes are present in an expression cassette.

4. The method according to claim 2, characterized in that the resistance genes are selected under tetracycline resistance or kanamycin resistance.

5. The method according to claim 2, characterized in that plasmid pMut1 is marked with a tetracycline resistance cassette and the sacB gene and that the original plasmid pMut2 is marked with a kanamycin resistance cassette and the sacB gene.

6. The method according to claim 5, in which the bacteria transformed with plasmid pMut1, that is marked with a tetracycline resistance cassette and the sacB gene, are cultivated on plates containing tetracycline and subsequently on plates containing saccharose, and that after elimination of plasmid pMut1 in the first step elimination of plasmid pMut2 takes place by cultivation on kanamycin plates and further cultivation on saccharose plates.

\* \* \* \* \*